US011278856B2

(12) United States Patent
Lu et al.

(10) Patent No.: US 11,278,856 B2
(45) Date of Patent: Mar. 22, 2022

(54) LUTEIN MICROCAPSULE FORMULATION AND PREPARATION METHOD THEREOF

(71) Applicant: CHENGUANG BIOTECH GROUP CO., LTD, Quzhou County (CN)

(72) Inventors: Qingguo Lu, Quzhou County (CN); Jianzhong Xu, Quzhou County (CN); Yunhe Lian, Quzhou County (CN)

(73) Assignee: CHENGUANG BIOTECH GROUP CO., LTD, Quzhou County (CN)

(*) Notice: Subject to any disclaimer, the term of this patent is extended or adjusted under 35 U.S.C. 154(b) by 43 days.

(21) Appl. No.: 15/547,052

(22) PCT Filed: Jan. 28, 2015

(86) PCT No.: PCT/CN2015/071749
§ 371 (c)(1),
(2) Date: Jul. 27, 2017

(87) PCT Pub. No.: WO2016/119143
PCT Pub. Date: Aug. 4, 2016

(65) Prior Publication Data
US 2018/0021749 A1  Jan. 25, 2018

(51) Int. Cl.
| | |
|---|---|
| *B01J 13/08* | (2006.01) |
| *A61K 31/047* | (2006.01) |
| *A23L 33/105* | (2016.01) |
| *A23K 20/179* | (2016.01) |
| *A23L 33/10* | (2016.01) |
| *A61K 9/50* | (2006.01) |
| *A61K 47/14* | (2017.01) |
| *A61K 47/22* | (2006.01) |
| *A61K 47/26* | (2006.01) |
| *A61K 47/46* | (2006.01) |

(52) U.S. Cl.
CPC .............. *B01J 13/08* (2013.01); *A23K 20/179* (2016.05); *A23L 33/10* (2016.08); *A23L 33/105* (2016.08); *A61K 9/5036* (2013.01); *A61K 9/5089* (2013.01); *A61K 31/047* (2013.01); *A61K 47/14* (2013.01); *A61K 47/22* (2013.01); *A61K 47/26* (2013.01); *A61K 47/46* (2013.01); *A23V 2002/00* (2013.01)

(58) Field of Classification Search
None
See application file for complete search history.

(56) References Cited

U.S. PATENT DOCUMENTS

2012/0009168 A1\*  1/2012  Wang ..................... A61K 9/107
424/94.1

FOREIGN PATENT DOCUMENTS

| CN | 1545923 A | | 11/2004 | |
|---|---|---|---|---|
| CN | 101023140 A | | 8/2007 | |
| CN | 101433528 A | | 5/2009 | |
| CN | 101177540 B | | 4/2010 | |
| CN | 102258499 A | | 11/2011 | |
| CN | 102389108 A | | 3/2012 | |
| CN | 103406079 A | | 11/2013 | |
| CN | 103565778 A | \* | 2/2014 | |
| CN | 103735532 A | \* | 4/2014 | |
| CN | 103735616 A | | 4/2014 | |
| CN | 103406079 B | \* | 7/2016 | |
| WO | WO-2008000534 A1 | \* | 1/2008 | ............... A23L 2/52 |

OTHER PUBLICATIONS

CN 102389108 A, English machine translation, 2013 (Year: 2013).\*
Hui Bozhen, Carotenoid Chemistry and Biochemistry, 2005, pp. 248 & 257, China Light Industry Press, Beijing.
Javier D. L. Rivas, Reversed-phase high performance liquid chromatographic separation of lutein and lutein fatly acid esters from marigold flower petal powder, Journal of Chromatography, 1989, pp. 442-447, 464, Elsevier Science Publishers B.V., Amsterdam.

\* cited by examiner

*Primary Examiner* — Susan T Tran
*Assistant Examiner* — William Craigo
(74) *Attorney, Agent, or Firm* — Morgan, Lewis & Bockius LLP

(57) ABSTRACT

A lutein microcapsule formulation and preparation method thereof, the formulation comprising the following ingredients: lutein crystals, a water-soluble emulsifier, an oil-soluble antioxidant, a wall material, a filler, a water-soluble antioxidant, and purified water. The preparation method comprises: dissolving the lutein crystals and the oil-soluble antioxidant in the water-soluble emulsifier to obtain an oil phase; adding the wall material, the water-soluble antioxidant, and the filler to the purified water to obtain a water phase; adding the oil phase to the water phase, grinding to obtain a particle size of the liquid emulsion of less than 100 nm, and granulating.

15 Claims, No Drawings

LUTEIN MICROCAPSULE FORMULATION AND PREPARATION METHOD THEREOF

TECHNICAL FIELD

The present invention relates to the carotenoid microcapsule technology, and in particular to a lutein microcapsule formulation and preparation method thereof.

BACKGROUND ART

Lutein, also known as dihydroxy-d-carotene, 9-carotene-3,3'-diol, is an oxygen-containing carotenoid, and it has a variety of physiological functions in addition to being used as a colorant, such as antioxidation, eliminating free radicals, anticancer, reducing the incidence of cardiovascular diseases and protecting vision, and especially receives widespread concern in the aspects such as the prevention of senile cataract and age-related macular degeneration. Lutein is widely distributed in bananas, kiwi, corn, marigold and other plants. Lutein used in the food industry, feed industry and the pharmaceutical industry is generally extracted from marigold, and usually exists in esterified form with fatty acids such as myristic acid, lauric acid and palmitic acid. Esterified lutein needs to be converted into free lutein such that it can be metabolized by human body.

Free lutein means that lutein crystal is very unstable, very sensitive to light and oxygen, easily oxidized and decomposed, and insoluble in water, which greatly limits its applications in food, medicine and feed industries.

Microcapsule technology is an effective method to solve the above-mentioned problems. Since the lutein is wrapped in a tiny capsule formed by a continuous capsule material, direct exposure to the environment is avoided, and its stability during storage, transportation and use is maintained.

The reports relating to the lutein microencapsulation or the similar formulations include the followings:

CN200580031802.8 (CN101023140A) relates to a process for producing a dry powder of at least one carotenoid, comprising dispersing at least one carotenoid in an aqueous molecular solution or colloidal solution of a mixture formed by isomalt and at least one protective colloid, then separating water, optionally adding a solvent, and then drying to convert the formed dispersion into dry powder. The dry powder obtained by this method has poor stability and cannot meet the requirements of the market.

CN200810137559.3 (CN101433528A) relates to a method for preparing stable aqueous dispersion of lutein microcapsule from lutein crystal. The method adopts instantaneous high temperature melting method to dissolve lutein crystal in edible oil, emulsifying matrix is added for emulsification, and the active compounds are homogenized by high pressure homogenizer to obtain lutein solution. The lutein solution is granulated and coated by a fluidized bed, and the coating carrier is subjected to droplet surface adsorption, and then cooled and shaped. The method is closely related to the present invention. The lutein microcapsule prepared by the method has a particle diameter of 5 to 40 µm which does not reach nanometer scale, and it cannot reach clear and transparent effects when being dispersed in water. Furthermore, a large amount of edible oil is required, and thus it is impossible to prepare microcapsules with a high content. In addition, the prepared microcapsule has a small proportion of the wall material under the conditions of the same content, so a poor stability is provided.

CN201110232047.7 (CN102258499A) discloses a method for preparing lutein microcapsules. The method comprises the steps of: melting a lutein powder in medicinal soybean oil by high-temperature melting method to prepare a mixed core material solution, mixing a wall material solution with the mixed core material solution, forming a primary emulsion by high-speed shearing, then preparing lutein emulsion using high-pressure homogenizer, and allowing the emulsion to be spray dried to obtain the lutein microcapsule. The preparation method needs a large amount of edible oil and emulsifiers, and thus it is impossible to prepare microcapsules with a high content. In addition, the prepared microcapsule has a small proportion of the wall material under the conditions of the same content, so a poor stability is provided.

CN200610154617.4 (CN101177540B) relates to a preparation method of food-grade water-soluble dry powder of lutein, comprising the steps of: mixing the lutein crystal with an organic solvent which has a low boiling point, volatile property and good ability to dissolve lutein crystal, heating and dissolving to obtain an oil phase, mixing and emulsifying with the water phase, then followed by performing high-pressure homogenization, removing the organic solvent in the emulsion system by the conventional separation method, and removing the moisture in the emulsion by spray drying method to obtain dry powder. The preparation method uses an organic solvent to dissolve the lutein crystal, and the solvent residue cannot be avoided though the organic solvent with low boiling point and volatile property is used. In addition, a large amount of organic solvents are used, and the recovery of the solvents results in the consumption of certain energy.

CN201310392763.0 (CN103406079A) discloses a method comprising suspending carotenoid crystals in an aqueous solution containing antioxidant, protective colloid and at least one nonionic emulsifier, grinding and homogenizing under nitrogen protection, and then dehydrating and drying to form powdered particles. The lutein microcapsules prepared according to the invention have certain dispersibility, but the transparency of the aqueous dispersion is poor since the lutein crystals cannot be dissolved in the emulsifier, which cannot meet the high-end requirements.

Therefore, there is a need to provide a lutein formulation having a high stability and good water solubility.

SUMMARY OF THE INVENTION

The technical problem to be solved by the present invention is to overcome the drawbacks of the prior art described above, and to provide a highly stable lutein microcapsule formulation which is easy to be industrially produced and provided with a shape of microsphere.

The present invention provides a lutein microcapsule formulation comprising the following ingredients: lutein crystals, oil soluble antioxidant, water-soluble emulsifier, wall material, filler, water-soluble antioxidant and purified water.

Specifically, the formulation comprises the following ingredients in parts by weight: 1 part of lutein crystal, 0.1-0.5 parts of oil-soluble antioxidant, 0.3-1.0 parts of water-soluble emulsifier, 3.0-4.0 parts of wall material, 4.0-5.0 parts of filler, 0.2-1.0 parts of water-soluble antioxidant, and 8.0-12.5 parts of purified water.

Preferably, the formulation comprises the following ingredients in parts by weight: 1 part of lutein crystal, 0.1-0.3 parts of oil-soluble antioxidant, 0.5-1.0 parts of water-soluble emulsifier, 3.5-3.75 parts of wall material, 4.5-4.75 parts of filler, 0.5-0.8 parts of water-soluble antioxidant, and 10-11.5 parts of purified water.

In the above-mentioned formulation:

The lutein crystals are commercially available, wherein the lutein content is 80% or more;

The oil-soluble antioxidant is a natural vitamin E or rosemary extract, wherein the rosemary extract is a natural antioxidant extracted from the plant rosemary, and the content of the active ingredient carnosic acid is not less than 20%;

The water-soluble emulsifier is a water-soluble emulsifier having an HLB value of 13 or more, and it is preferably one or two of polyglycerol fatty acid ester, sucrose fatty acid ester, and polyoxyethylene sorbitan fatty acid ester.

The polyoxyethylene sorbitan fatty acid ester is polysorbate-80.

The wall material is one or two of acacia and octenyl succinate starch ester.

The filler is one or two of iso-maltol, sucrose and glucose.

The water-soluble antioxidant is a mixture of ascorbic acid and tea polyphenol or a mixture of ascorbic acid and oligomeric procyanidin. Preferably the weight ratio of ascorbic acid to tea polyphenol is 1:1; and the weight ratio of ascorbic acid to oligomeric procyanidin is 1:1.

Another purpose of the present invention is to provide a preparation method of the above microcapsule formulation, comprising the steps of:

1) melting the lutein crystal in the water-soluble emulsifier which is added with the oil-soluble antioxidant to obtain an oil phase;

2) adding the wall material, the water-soluble antioxidant and the filler into purified water at 50-80° C., and then stirring and dissolving to obtain a water phase; and 3) adding the oil phase into the water phase and stirring well, then coarse grinding through a colloid mill, and fine grinding through a sand mill such that the ground emulsion particles have a particle diameter of 100 nm or less, and allowing the emulsion to be one-step granulated by a spray-starch fluidized bed drying process to obtain a spherical microcapsule formulation having a particle diameter of 40 mesh to 100 mesh.

Preferably, the method comprises the steps of:

1) melting the lutein crystal at 140° C.-180° C. in the water-soluble emulsifier which is added with the oil-soluble antioxidant to obtain an oil phase;

2) adding the wall material, the water-soluble antioxidant and the filler into the purified water at 50-80° C., and then stirring and dissolving for 30-60 minutes to obtain a water phase; and 3) adding the oil phase into the water phase and stirring well, then coarse grinding through a colloid mill, and fine grinding through a sand mill whose grinding medium has a particle diameter of 0.5-1.0 mm and which has a rotation speed of 1500-2000 rpm, such that the ground emulsion particles have a particle diameter of 100 nm or less, and then allowing the emulsion to be one-step granulated by a spray-starch fluidized bed drying process to obtain a spherical microcapsule formulation having a particle diameter of 40 mesh to 100 mesh.

In the above method:

During the spray-starch fluidized bed drying process, the binder used is water-soluble starch, the inlet air temperature for spraying is 110-130° C., and the blast temperature of the starch fluidized bed is 60-80° C.

The lutein microcapsule formulation provided by the present invention has the following advantages:

1. With regard to the lutein microcapsule formulation and the preparation method thereof provided by the present invention, organic solvent is not used in the raw materials and during the whole preparation process, which improves the safety of the product; the lutein crystal is melted in the water-soluble emulsifier without using the edible oil, after in combination with further grinding, it allows the microcapsules to have a particle diameter of 100 nm or less, so that the aqueous dispersion of the product is clear and transparent; by using starch for one-step granulation to obtain spherical microcapsule, the effect of secondary embedding can be achieved to improve the stability, and the drawbacks of the powder prepared by the spray drying method, such as poor resistance to pressure, unsuitability for tabletting (poor fluidity), and unsuitability for filling hard capsules can be overcome.

2. Stability test: the microcapsule formulation provided by the present invention has a content retention rate of more than 97% after standing under the conditions of 40° C. and RH 75% for 6 months.

SPECIFIC MODES FOR CARRYING OUT THE EMBODIMENTS

The following examples are intended to illustrate the invention, but not intended to limit the scope of the invention.

The rosemary extract is a natural antioxidant extracted from the plant rosemary, wherein the content of the active ingredient carnosic acid is not less than 20%. The rosemary extract is purchased from Henan Senyuan Herbary Natural Products Co., Ltd.

Example 1: Lutein Microcapsule Formulation 1. 20 g of lutein crystals with a lutein content of 80% and 2 g of rosemary extract (about 0.1 times of lutein) were added to 20 g of polyglycerol fatty acid ester (about 1 time of lutein), heated to 165° C. and kept for 5 min until they were completely melted to obtain an oil phase, wherein the vessel for melting was protected by nitrogen.

2. 75 g of acacia (about 3.75 times of lutein), 95 g of iso-maltol (about 4.75 times of lutein), and a mixture of 5 g of ascorbic acids and 5 g of tea polyphenol (totaling about 0.5 times of lutein) were dissolved into 230 g of purified water (about 11.5 times of lutein) at 75° C. for 0.5 hours, and kept at the same temperature to give a water phase.

3. The oil phase at 165° C. was slowly added into the water phase at 75° C. under shear stirring with a rotation speed of >10000rpm, stirred for 0.5 hour, and then cooled to room temperature to obtain a mixed liquor.

4. The mixed liquor was passed through a colloid mill, and then ground by a sand mill at a speed of 1900 rpm for 0.5 hours. The detection result of the particle diameter is 95 nm.

5. The mixed liquor was granulated by spray-starch fluidized bed drying after being ground, wherein inlet air temperature for spraying was 120° C., and the blast temperature of the starch fluidized bed was 75° C. 270 g lutein microcapsule formulation with the lutein content of 5% was obtained.

Example 2: Lutein Microcapsule Formulation 1. 40 kg of lutein crystals with a lutein content of 80% and 4 kg of rosemary extract (about 0.1 times of lutein) were added to 40 kg of polysorbate-80 (about 1 time of lutein), heated to 160° C. and kept for 10 min until they were completely melted to obtain an oil phase, wherein the vessel for melting was protected by nitrogen.

2. 150 kg of acacia (about 3.75 times of lutein), 190 kg of sucrose (about 4.75 times of lutein), and a mixture of 10 kg of ascorbic acids and 10 kg of oligomeric procyanidin (totaling about 0.5 times of lutein) were dissolved into 450 kg of purified water (about 11.25 times of lutein) at 70° C. for 45 min, and kept at the same temperature to give a water phase.

3. The oil phase at 160° C. was slowly added into the water phase at 75° C. under shear stirring with a rotation speed of ≥10000rpm, stirred for 0.5 hour, and then cooled to room temperature to obtain a mixed liquor.

4. The mixed liquor was passed through a colloid mill, and then ground by a sand mill at a speed of 2000 rpm for 1 hour. The detection result of the particle diameter is 90 nm.

5. The mixed liquor was granulated by spray-starch fluidized bed drying after being ground, which gives 540 kg lutein microcapsule formulation with the lutein content of 5%.

Example 3: Lutein Microcapsule Formulation 1. 27 kg of lutein crystals with a lutein content of 80% and 3 kg of vitamin E (about 0.11 times of lutein) were added to 27 kg of sucrose fatty acid ester (about 1 time of lutein), heated to 170° C. and kept for 10 min until they were completely melted to obtain an oil phase, wherein the vessel for melting was protected by nitrogen.

2. 100 kg of octenyl succinate starch ester (about 3.70 times of lutein), 128 kg of sucrose (about 4.74 times of lutein), and a mixture of 7.5 kg of ascorbic acids and 7.5 kg of tea polyphenol (totaling about 0.56 times of lutein) were dissolved into 300 kg of purified water at 70° C. for 45 min, and kept at the same temperature to give a water phase.

3. The oil phase at 170° C. was slowly added into the water phase at 75° C. under shear stirring with a rotation speed of ≥10000rpm, stirred for 0.5 hour, and then cooled to room temperature to obtain a mixed liquor.

4. The mixed liquor was passed through a colloid mill, and then ground by a sand mill at a speed of 1800 rpm for 1 hour. The detection result of the particle diameter is 100 nm.

5. The mixed liquor was granulated by spray-starch fluidized bed drying after being ground, which gives 360 kg lutein microcapsule formulation with the lutein content of 5%.

Experimental Example: Investigation of Stability and Water Solubility

1. Samples: the microcapsules of Examples 1-3, the microcapsules of Comparative Examples 1-5, wherein:

Comparative Example 1 prepared according to the method provided in Example 1 of CN200580031802.8 (CN101023140A);

Comparative Example 2 prepared according to the method provided in Example 1 of CN200810137559.3 (CN101433528A);

Comparative Example 3 prepared according to the method provided in Example 1 of CN201110232047.7 (CN102258499A);

Comparative Example 4 prepared according to the method provided in Example 1 of CN200610154617.4 (CN101177540B); and Comparative Example 5 prepared according to the method provided in Example 6 of CN201310392763.0 (CN103406079A).

2. Investigation methods:

Stability: the lutein microcapsules prepared in Examples 1-3 and Comparative Examples 1-5 were placed directly in a drug stability test chamber, kept under the conditions of 40° C. and RH 75% in dark and then measured for the initial contents of the samples and the contents after being kept for 6 months, and then the content retention rate was calculated.

Water solubility: 0.1000 g of lutein microcapsule sample was weighed and placed in a 100 ml volumetric flask, added with purified water for dissolving (ultrasonic treatment was conducted if necessary,), and diluted with purified water to 100 ml. A black and white pattern similar to a Secchi's disc was attached to the bottom of a 50 ml colorimetric tube, then the dissolved sample was poured into the colorimetric tube until the pattern at the bottom could not be seen clearly, and the height of the liquid level in the colorimetric tube was recorded at this time point. The test was repeated for three times, and the average value was calculated.

3. The test results are shown in Table 1.

TABLE 1

Test results

| | The content retention rates (%) after standing under the conditions of 40° C. and RH 75% for 6 months | Transparency (cm) |
|---|---|---|
| Example 1 | 98.2 | 13.75 |
| Example 2 | 98.0 | 13.80 |
| Example 3 | 97.9 | 14.05 |
| Comparative Example 1 | 78.8 | 8.6 |
| Comparative Example 2 | 82.4 | 11.2 |
| Comparative Example 3 | 85.6 | 13.2 |
| Comparative Example 4 | 95.2 | 13.5 |
| Comparative Example 5 | 92.5 | 9.2 |

The results in Table 1 showed that, the retention rates of the microcapsules after standing for 6 months were 97% or more of Examples 1-3, while the highest retention rate of the microcapsules of Comparative Examples 1-5 was 92.5%, which is lower than those of Examples 1-3; and the transparencies of the microcapsules of Examples 1-3 were 13.7 cm or more, and the highest transparency of the microcapsules of Comparative Examples was 13.5 cm.

The results showed that: the stability of the lutein microcapsules provided by the present invention was superior to that of the comparative patent applications, and the transparency of the aqueous dispersion also ranked in upper level, which can meet the actual production needs.

INDUSTRIAL APPLICABILITY

The invention provides a highly stable lutein microcapsule formulation which is easy to be industrially produced and provided with a shape of microsphere. The formulation and the preparation method thereof do not use the organic solvent, which improves the safety of the product; the lutein crystal is melted in the water-soluble emulsifier without using the edible oil, after in combination with further grinding, it allows the microcapsules to have a particle diameter of 100 nm or less, so that the aqueous dispersion of the product is clear and transparent; by using starch for one-step granulation to obtain spherical microcapsule, the effect of secondary embedding can be achieved to improve the stability, and the drawbacks of the powder prepared by the spray drying method, such as poor resistance to pressure, unsuitability for tabletting (poor fluidity), and unsuitability for filling hard capsules can be overcome.

What is claimed is:

1. A lutein microcapsule formulation comprising lutein, wherein the lutein microcapsule formulation is prepared from raw materials comprising the following ingredients in parts by weight: 1 part of lutein in crystal form, 0.1-0.5 parts of oil-soluble antioxidant, 0.3-1.0 parts of water-soluble emulsifier, 3.0-4.0 parts of wall material, 4.0-5.0 parts of filler, 0.2-1.0 parts of water-soluble antioxidant, and 8.0-12.5 parts of purified water,
   wherein the lutein microcapsule formulation is prepared by a method comprising:
   1) melting the lutein, of the raw materials, in the water-soluble emulsifier which is added with the oil-soluble antioxidant to obtain an oil phase;
   2) adding the wall material, the water-soluble antioxidant and the filler into the purified water at 50-80 ° C., and then stirring and dissolving to obtain a water phase; and
   3) adding the oil phase into the water phase and stirring, then coarse grinding through a colloid mill, and fine grinding through a sand mill,
   wherein when the lutein microcapsule formulation is dispersed in water in combination with the coarse grinding, lutein microcapsules having a particle diameter of 100 nm or less are produced, and
   wherein when the lutein microcapsule formulation is placed in a chamber for six months under conditions of 40 ° C. and RH 75%, the lutein microcapsule formulation has a content retention rate of 97% or higher.

2. The formulation according to claim 1, characterized in that, the raw materials comprise the following ingredients in parts by weight: 1 part of lutein in crystal form, 0.1-0.3 parts of oil-soluble antioxidant, 0.5-1.0 parts of water-soluble emulsifier, 3.5-3.75 parts of wall material, 4.5-4.75 parts of filler, 0.5-0.8 parts of water-soluble antioxidant, and 10-11.5 parts of purified water.

3. The formulation according to claim 1, characterized in that, the oil-soluble antioxidant is natural vitamin E or rosemary extract.

4. The formulation according to claim 1, characterized in that, the water-soluble emulsifier has an HLB value of 13 or more, and comprises one or more water-soluble emulsifier selected from the group consisting of polyglycerol fatty acid ester, sucrose fatty acid ester, polysorbate-80, polyoxyethylene sorbitan fatty acid ester, and combinations thereof.

5. The formulation according to claim 1, characterized in that, the wall material is one or two of acacia and octenyl succinate starch ester.

6. The formulation according to claim 1, characterized in that, the filler is one or two of iso-maltol, sucrose and glucose.

7. The formulation according to claim 1, characterized in that, the water-soluble antioxidant is a mixture of ascorbic acid and tea polyphenol or a mixture of ascorbic acid and oligomeric procyanidin.

8. The formulation according to claim 2, characterized in that, the oil-soluble antioxidant is natural vitamin E or rosemary extract.

9. The formulation according to claim 2, characterized in that, the water-soluble emulsifier has an HLB value of 13 or more, and comprises one or more water-soluble emulsifier selected from the group consisting of polyglycerol fatty acid ester, sucrose fatty acid ester, polysorbate-80, polyoxyethylene sorbitan fatty acid ester, and combinations thereof.

10. The formulation according to claim 2, characterized in that, the wall material is one or two of acacia and octenyl succinate starch ester.

11. The formulation according to claim 2, characterized in that, the filler is one or two of iso-maltol, sucrose and glucose.

12. The formulation according to claim 1, wherein when 0.1000g of the lutein microcapsule formulation is placed in a 100 ml volumetric flask, added with purified water for dissolving, and diluted with purified water to 100 ml to create a sample, when a black and white pattern of a Secchi disc is attached to a bottom of a 50 ml colorimetric tube, and when the sample is poured into the 50 ml colorimetric tube until the black and white pattern at the bottom becomes invisible, a height of a liquid level in the 50 ml colorimetric tube is 13.7 cm or more.

13. The formulation according to claim 1, wherein melting the lutein comprises melting the lutein at 160-180 ° C.

14. A preparation method of the formulation according to claim 1, characterized in that, the method comprises the steps of:
   1) melting the lutein crystal in the water-soluble emulsifier which is added with the oil-soluble antioxidant to obtain an oil phase;
   2) adding the wall material, the water-soluble antioxidant and the filler into the purified water at 50-80° C., and then stirring and dissolving to obtain a water phase; and
   3) adding the oil phase into the water phase and stirring well, then coarse grinding through a colloid mill, and fine grinding through a sand mill such that the ground emulsion particles have a particle diameter of 100 nm or less, and allowing the emulsion to be one-step granulated by a spray-starch fluidized bed drying process to obtain a spherical microcapsule formulation having a particle diameter of 40 mesh to 100 mesh.

15. The method according to claim 14, characterized in that, the method comprises the steps of:
   1) melting the lutein crystal at 140° C. -180° C. in the water-soluble emulsifier which is added with the oil-soluble antioxidant to obtain an oil phase;
   2) adding the wall material, the water-soluble antioxidant and the filler into the purified water at 50-80° C., and then stirring and dissolving for 30-60 minutes to obtain a water phase; and
   3) adding the oil phase into the water phase and stirring well, then coarse grinding through a colloid mill, and fine grinding through a sand mill whose grinding medium has a particle diameter of 0.5-1.0 mm and which has a rotation speed of 1500-2000 rpm, such that the ground emulsion particles have a particle diameter of 100 nm or less, and then allowing the emulsion to be one-step granulated by a spray-starch fluidized bed drying process to obtain a spherical microcapsule formulation having a particle diameter of 40 mesh to 100 mesh.

* * * * *